United States Patent
Allen et al.

(10) Patent No.: US 9,498,131 B1
(45) Date of Patent: Nov. 22, 2016

(54) AIDS FOR MAINTAINING SCHEDULED MEDICATION DOSING

(71) Applicant: International Business Machines Corporation, Armonk, NY (US)

(72) Inventors: Ira L. Allen, Dallas, TX (US); Gregory J. Boss, Saginaw, MI (US); Andrew R. Jones, Round Rock, TX (US); Kevin C. McConnell, Austin, TX (US); John E. Moore, Jr., Brownsburg, IN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/801,368

(22) Filed: Jul. 16, 2015

(51) Int. Cl.
*A61B 5/00* (2006.01)
*G06K 7/10* (2006.01)
*A61B 5/07* (2006.01)

(52) U.S. Cl.
CPC .............. *A61B 5/0031* (2013.01); *A61B 5/076* (2013.01); *A61B 5/4205* (2013.01); *A61B 5/4833* (2013.01); *A61B 90/98* (2016.02); *G06K 7/10366* (2013.01); *A61B 5/4839* (2013.01)

(58) Field of Classification Search
CPC .. A61B 5/0031; A61B 5/076; A61B 5/4205; A61B 5/4839; A61B 5/4833; A61B 5/073; A61B 5/04012; A61B 5/04525; A61B 90/98; G06Q 50/00; G08B 1/08; G08B 23/00; G06B 19/3462; G06K 2017/0045; G06K 7/0366; G06F 19/3468; G06F 19/323
USPC .......... 340/573.1, 10.1, 572.1, 10.4; 600/302
See application file for complete search history.

(56) References Cited

U.S. PATENT DOCUMENTS

| | | | |
|---|---|---|---|
| 8,269,636 B2 | 9/2012 | Kroll et al. | |
| 8,727,180 B2 * | 5/2014 | Zonana | B65D 83/0409 221/195 |
| 9,047,746 B1 * | 6/2015 | Euliano, II | G08B 23/00 |

(Continued)

FOREIGN PATENT DOCUMENTS

| | | |
|---|---|---|
| CN | 101010114 A | 8/2007 |
| CN | 101695443 A | 4/2010 |
| WO | 2006055892 A2 | 5/2006 |

OTHER PUBLICATIONS

"Medication monitoring for elderly people through device implanted in permanent denture" https://priorartip.com/IPCOM/000238665; Sep. 2014.

Rajagopalan et al. "Ingestible RFID Bio-capsule Tag Design for Medical Monitoring"; Antennas and Propagation Society International Symposium (APSURSI), 2010 IEEE; Jul. 2010.

*Primary Examiner* — Ali Neyzari
(74) *Attorney, Agent, or Firm* — Brown & Michaels, PC; John R. Pivnichny

(57) ABSTRACT

Monitoring administration of medication to a user by receiving an identification of at least a medication and a time of administration of the medication to the user from the first sensor and storing the identification in the repository. The identification of the medication is compared to prescribed medication for the user. A time required for the medication to travel from the first location to the second location is determined. An electronic tag at the second location is monitored until the determined time has passed or the electronic tag is identified. When the determined time has passed and an electronic tag has not been identified, a notification is sent to at least one user; and when the electronic tag is identified, the ingestion of the medication is confirmed by the user and the time and electronic tag identification is stored in the repository.

20 Claims, 5 Drawing Sheets

(56) References Cited

U.S. PATENT DOCUMENTS

| | | |
|---|---|---|
| 2005/0285746 A1 | 12/2005 | Sengupta et al. |
| 2009/0009332 A1 | 1/2009 | Nunez et al. |
| 2011/0163871 A1 | 7/2011 | Einav et al. |
| 2013/0200033 A1 | 8/2013 | Zonana et al. |
| 2014/0309505 A1 | 10/2014 | Euliano et al. |
| 2015/0001285 A1* | 1/2015 | Halbert ............... G06F 19/3468 235/375 |

\* cited by examiner

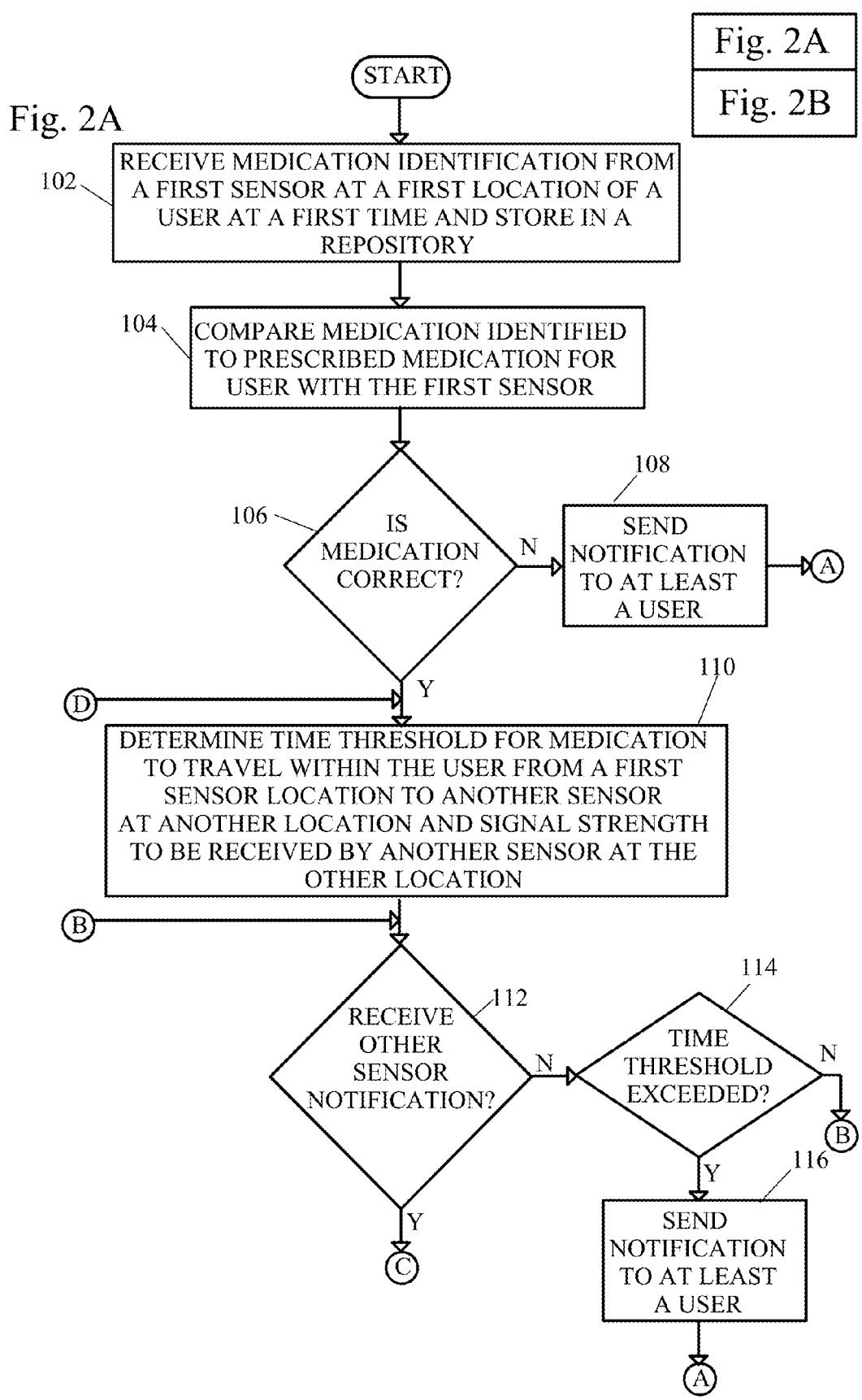

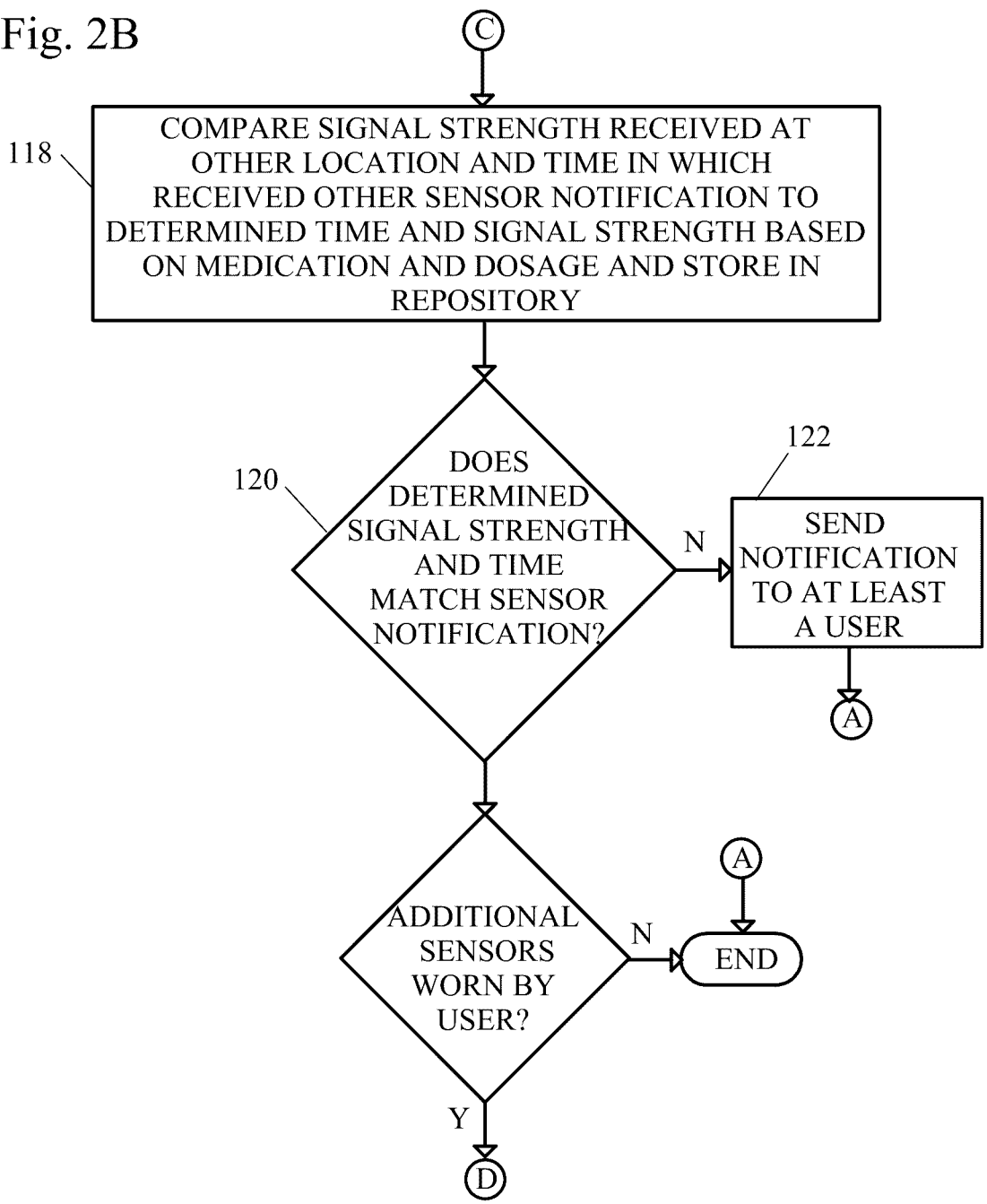

AIDS FOR MAINTAINING SCHEDULED MEDICATION DOSING

BACKGROUND

The present invention relates to scheduled medication dosing, and more specifically to aids in maintaining the scheduled medication dosing of users.

A common problem in medical facilities such as hospitals and nursing or care facilities is tracking whether or not a person actually receives prescribed medication, or whether or not they swallow the medication if they do receive it. Some users will not receive the medication they were prescribed, while of those that do, almost half of the users will not actually swallow the medication. Failure to adequately dispense and administer medication to users in the proper dosages is responsible for significant healthcare expenditures such as hospital admittance, unneeded medication changes, repeat doctor office visits, unexplained treatment failures, and admission to a skilled nursing facility.

SUMMARY

According to one embodiment of the present invention, a method of monitoring medication and administration of medication to a user containing edible electronic tags through the use of at least a first sensor at a first location and a second sensor at a second location different than the first location is disclosed. The first sensor and second sensor each comprise: one or more memories, an electronic tag reader, and at least one antenna, at least one of the first and second sensors being coupled to communicate with a computer. The computer comprising: at least one processor, one or more memories, and a repository coupled to the processor. The method comprising the steps of: the computer receiving an identification of at least a medication and a time of administration of the medication to the user from the first sensor and storing the identification in the repository; the computer comparing the identification of the medication to prescribed medication for the user; the computer determining a time required for the medication to travel from the first location to the second location; the computer monitoring for the electronic tag at the second location until the determined time has passed or the electronic tag is identified; wherein when the determined time has passed and an electronic tag has not been identified, the computer sending a notification to at least one user; and wherein when the electronic tag is identified, the computer confirming ingestion of the medication by the user and storing the time and electronic tag identification to the repository.

According to another embodiment of the present invention, a computer program product for monitoring medication and administration of medication to a user containing edible electronic tags through the use of at least a first sensor at a first location and a second sensor at a second location different than the first location. The first sensor and second sensor each comprising: one or more memories, an electronic tag reader, and at least one antenna, at least one of the first and second sensors being coupled to communicate with a computer. The computer comprising: at least one processor, one or more memories, and a repository coupled to the processor, a computer readable storage medium having program instructions embodied therewith is disclosed. The program instructions executable by the computer to perform the method comprising: receiving, by the computer, an identification of at least a medication and a time of administration of the medication to the user from the first sensor and storing the identification in the repository; comparing, by the computer, the identification of the medication to prescribed medication for the user; determining, by the computer a time required for the medication to travel from the first location to the second location; monitoring, by the computer, for the electronic tag at the second location until the determined time has passed or the electronic tag is identified; wherein when the determined time has passed and an electronic tag has not been identified, the computer sending a notification to at least one user; and wherein when the electronic tag is identified, the computer confirming ingestion of the medication by the user and storing the time and electronic tag identification to the repository.

According to another embodiment of the present invention, a computer system for monitoring medication and administration of medication to a user containing edible electronic tags through the use of at least a first sensor at a first location and a second sensor at a second location different than the first location, the first sensor and second sensor each comprising: one or more memories, an electronic tag reader, and at least one antenna, at least one of the first and second sensors being coupled to communicate with a computer. The computer comprising: at least one processor, one or more memories, and a repository coupled to the processor, a computer readable storage medium having program instructions embodied therewith is disclosed. The program instructions executable by the computer to perform the program instructions comprising: receiving, by the computer, an identification of at least a medication and a time of administration of the medication to the user from the first sensor and storing the identification in the repository; comparing, by the computer, the identification of the medication to prescribed medication for the user; determining, by the computer a time required for the medication to travel from the first location to the second location; monitoring, by the computer, for the electronic tag at the second location until the determined time has passed or the electronic tag is identified; wherein when the determined time has passed and an electronic tag has not been identified, the computer sending a notification to at least one user; and wherein when the electronic tag is identified, the computer confirming ingestion of the medication by the user and storing the time and electronic tag identification to the repository.

BRIEF DESCRIPTION OF THE SEVERAL VIEWS OF THE DRAWINGS

FIGS. 2A-2B show a flow diagram of a method of monitoring medication administration.

DETAILED DESCRIPTION

Embodiments of the present invention allow a user who is taking a medication, or alternate users, such as users caring for the individual receiving the medication, to monitor administration, dosage, and ingestion of the medication.

In one embodiment, the user or alternate user registers the medications and associated dosages with a program, for example the medication monitor and notification program, that tracks ingestion of medication, and time of ingestion as received by the user. Additionally, dosage (strength) of the medication may also be monitored. The medication preferably includes electronic tagging with passive or active tags which can be identified using radio-frequency identification (RFID) or near field communication (NFC) sensors.

The user preferably wears at least two sensors in different regions of their body which can detect an electronic signature of the electronically tagged medication through a receiver or antenna. The sensors in the different regions provide input to a medication monitor and notification program and a processor which may be separate from the sensors. The distance between and/or placement of the sensors is preferably calibrated for each user and is used in determining the expected time in detecting the tagged medication from first ingestion and detection by the first sensors worn by the user to another sensor in a different location worn by the user. The input may include, but is not limited to, medication identification, time stamp, a time the medication is expected to be detected by the sensor, for example a time threshold, and dosage.

Based on the sensor's input, a determination can be made regarding whether the medication was taken and ingested by the user, not just when it was administered to the user. If a user did not ingest the medication or was administered a dosage which was not prescribed, a notification can be sent to the alternate user. Alternatively, the notification may be sent to the user or alternate user electronically for display on a computing device or television, computer monitor or other display. Alternatively, the notification may be broadcast to the user.

The sensor input may also be analyzed to determine whether the dosage is correct for the user, based on the time the medication is ingested and the time it takes to pass through the digestive system of the user, as determined by additional sensors.

Figure 1:
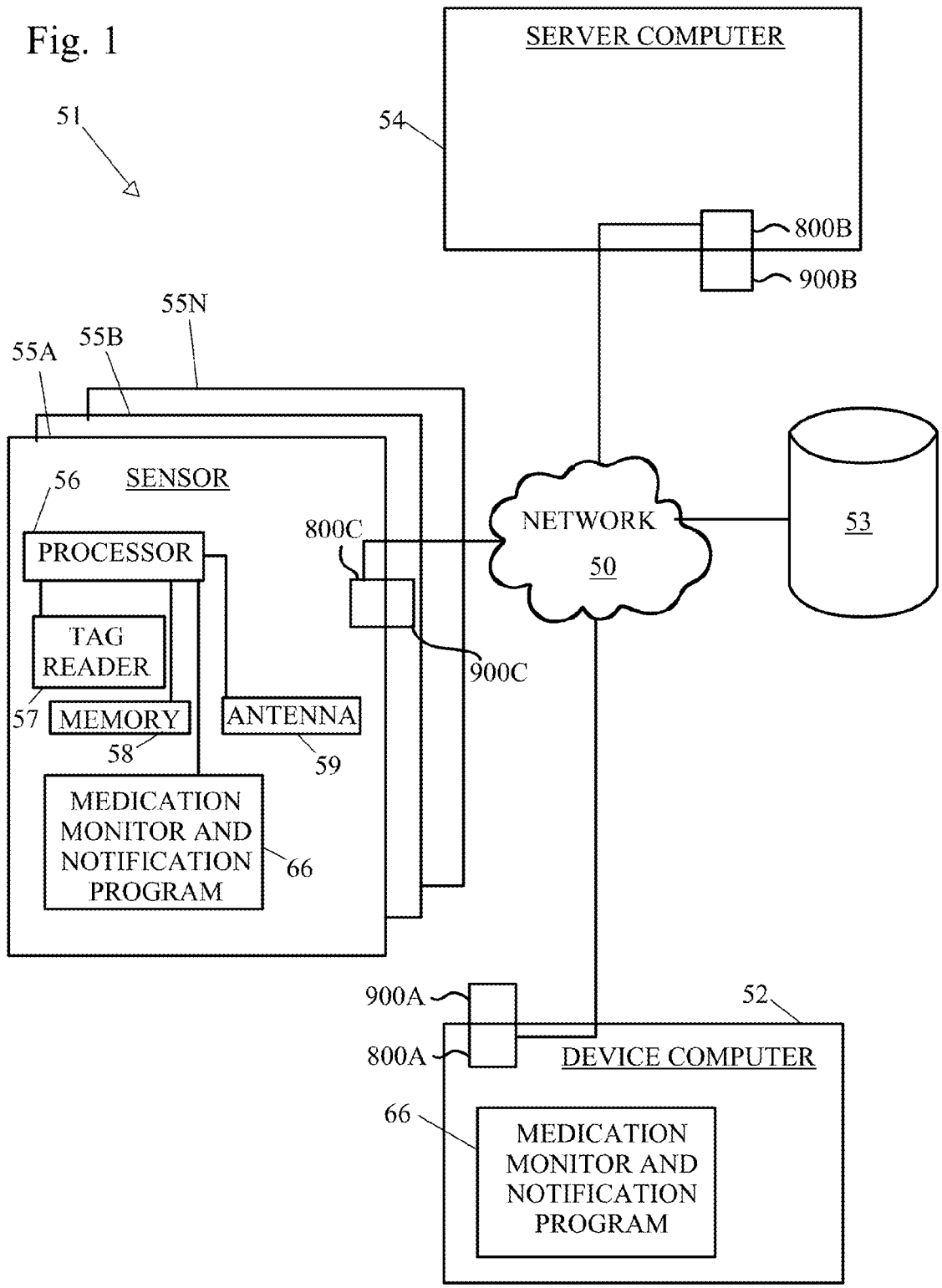
FIG. 1 depicts an exemplary diagram of a possible data processing environment in which illustrative embodiments may be implemented.

FIG. 1 is an exemplary diagram of a possible data processing environment provided in which illustrative embodiments may be implemented. It should be appreciated that FIG. 1 is only exemplary and is not intended to assert or imply any limitation with regard to the environments in which different embodiments may be implemented. Many modifications to the depicted environments may be made.

Referring to FIG. 1, network data processing system 51 is a network of computers in which illustrative embodiments may be implemented. Network data processing system 51 contains network 50, which is the medium used to provide communication links between various devices and computers connected together within network data processing system 51. Network 50 may include connections, such as wire, wireless communication links, or fiber optic cables.

In the depicted example, device computer 52, sensors 55a-55n, a repository 53, and a server computer 54 connect to network 50. In other exemplary embodiments, network data processing system 51 may include additional client or device computers, sensors, storage devices or repositories, server computers, and other devices not shown.

Sensors 55a-55n preferably each include an electronic tag reader 57 (preferably RFID or NFC), memory 58 for storing monitored data, one or more receivers or antennas 59 to communicate with the device computer 52. The sensors 55a-55n may also include a processor 56 as shown in FIG. 1 or alternatively, report any information to the device computer 52. The sensors 55a-55n are capable of at least monitoring for electronic tags and signal strength. The sensors 55a-55n may also determine the time for travel of the electronic tag between sensors at various locations, determine the strength of the signal between sensors at various locations, compare the time for travel to the determined amount of time and comparing the signal strength between sensors at various locations. The sensors 55a-55n preferably includes a medication monitor and notification program 66.

Figure 4:
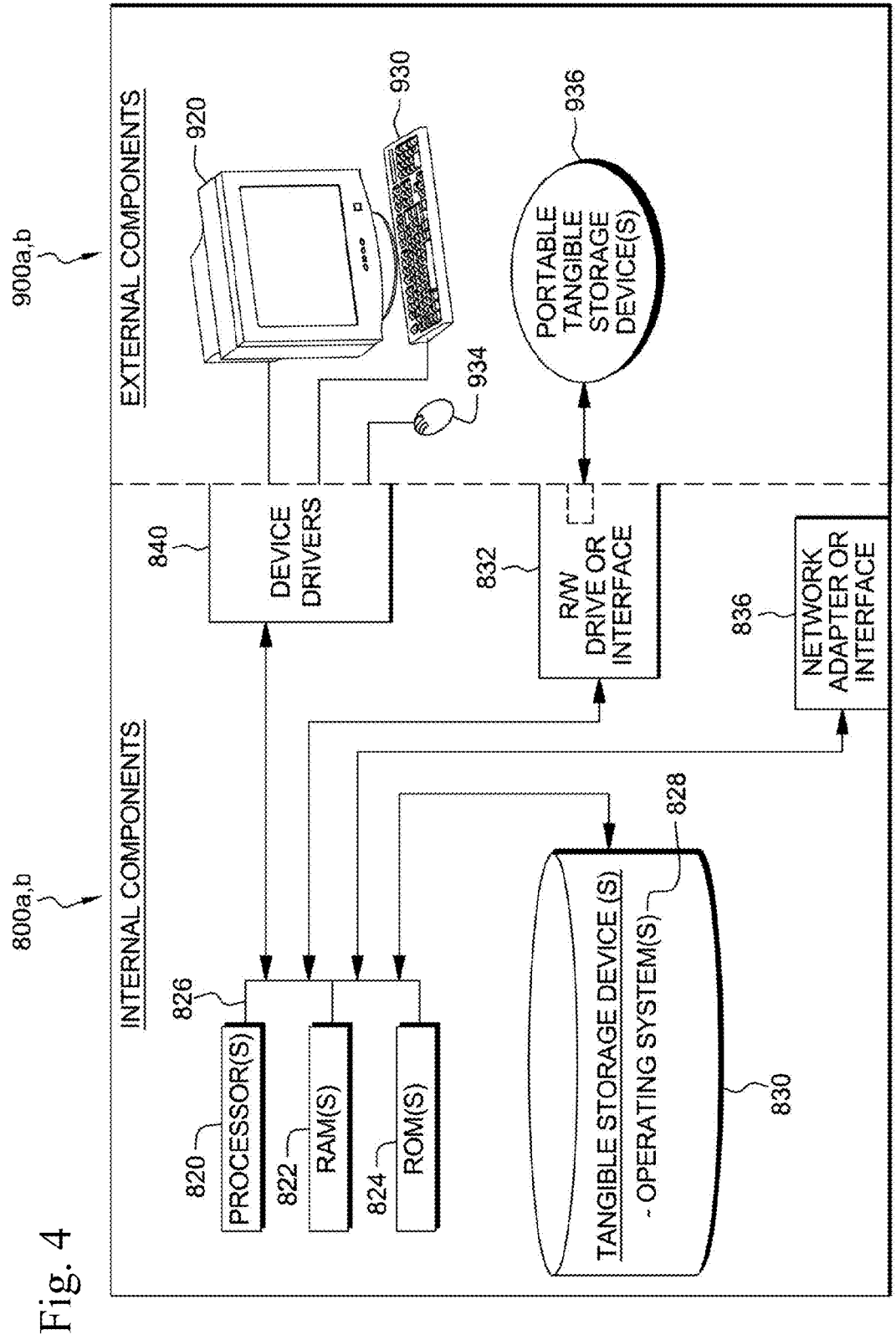
FIG. 4 illustrates internal and external components of a client or device computer and a server computer in which illustrative embodiments may be implemented.

Device computer 52 includes a set of internal components 800a and a set of external components 900a, further illustrated in FIG. 4. Device computer 52 may be, for example, a mobile device, a cell phone, a personal digital assistant, a netbook, a laptop computer, a tablet computer, a desktop computer, television, a wearable computer device, or any other type of computing device. The device computer 52 preferably able to receive input from the plurality of sensors 55a-55n. The device computer 52, based on the input from the sensors 55a-55n may also determine the time for travel of the electronic tag between sensors at various locations, determine the strength of the signal between sensors at various locations, compare the time for travel to the determined amount of time and comparing the signal strength between sensors at various locations.

Device computer 52 may contain an interface. The interface may accept commands and data entry from a user. The interface can be, for example, a command line interface, a graphical user interface (GUI), a web user interface (WUI), a natural user interface (NUI) or a touch user interface (TUI). The device computer 52 preferably includes a medication monitor and notification program 66. While not shown, it may be desirable to have the medication monitor and notification program 66 on the server computer 54.

Server computer 54 includes a set of internal components 800b and a set of external components 900b illustrated in FIG. 4. In the depicted example, server computer 54 provides information, such as boot files, operating system images, and applications to device computer 52. Server computer 54 can compute the information locally or extract the information from other computers on network 50.

Program code and programs such as a medication monitor and notification program 66 may be stored on at least one of one or more computer-readable tangible storage devices 830 shown in FIG. 4, on at least one of one or more portable computer-readable tangible storage devices 936 as shown in FIG. 4, on repository 53 connected to network 50, or downloaded to a data processing system or other device for use. For example, program code and programs such as medication monitor and notification program 66 may be stored on at least one of one or more tangible storage devices 830 on server computer 54 and downloaded to the device computer 52. Alternatively, server computer 54 can be a web server, and the program code and programs such as a medication monitor and notification program 66 may be stored on at least one of the one or more tangible storage devices 830 on server computer 54 and accessed on the device computer 52. Medication monitor and notification program 66 can be accessed on device computer 52 through an interface. In other exemplary embodiments, the program code and programs such as a medication monitor and notification program 66 may be stored on at least one of one or more computer-readable tangible storage devices 830 on server computer 54 or distributed between two or more servers.

FIGS. 2A-2B shows a flow diagram of a method of a method of monitoring medication administration and dosage.

It should be noted that prior to the steps of FIGS. 2A-2B, that at least some information regarding the user in which the medication is prescribed is inputted into a medication monitoring and notification program 66. The information may include, but is not limited to: user identification, medication, dosage, number of sensors, location of sensors, types of sensors, and other information. The sensors may be calibrated to a common receiver, which may be one of the other sensors or a separate computing device, which may additionally be wearable. It should be noted that at least two sensors is required to determine the difference between the two locations and the time ingested. The sensors are preferably worn by the user in such a way that is unobtrusive to the user.

Figure 3:
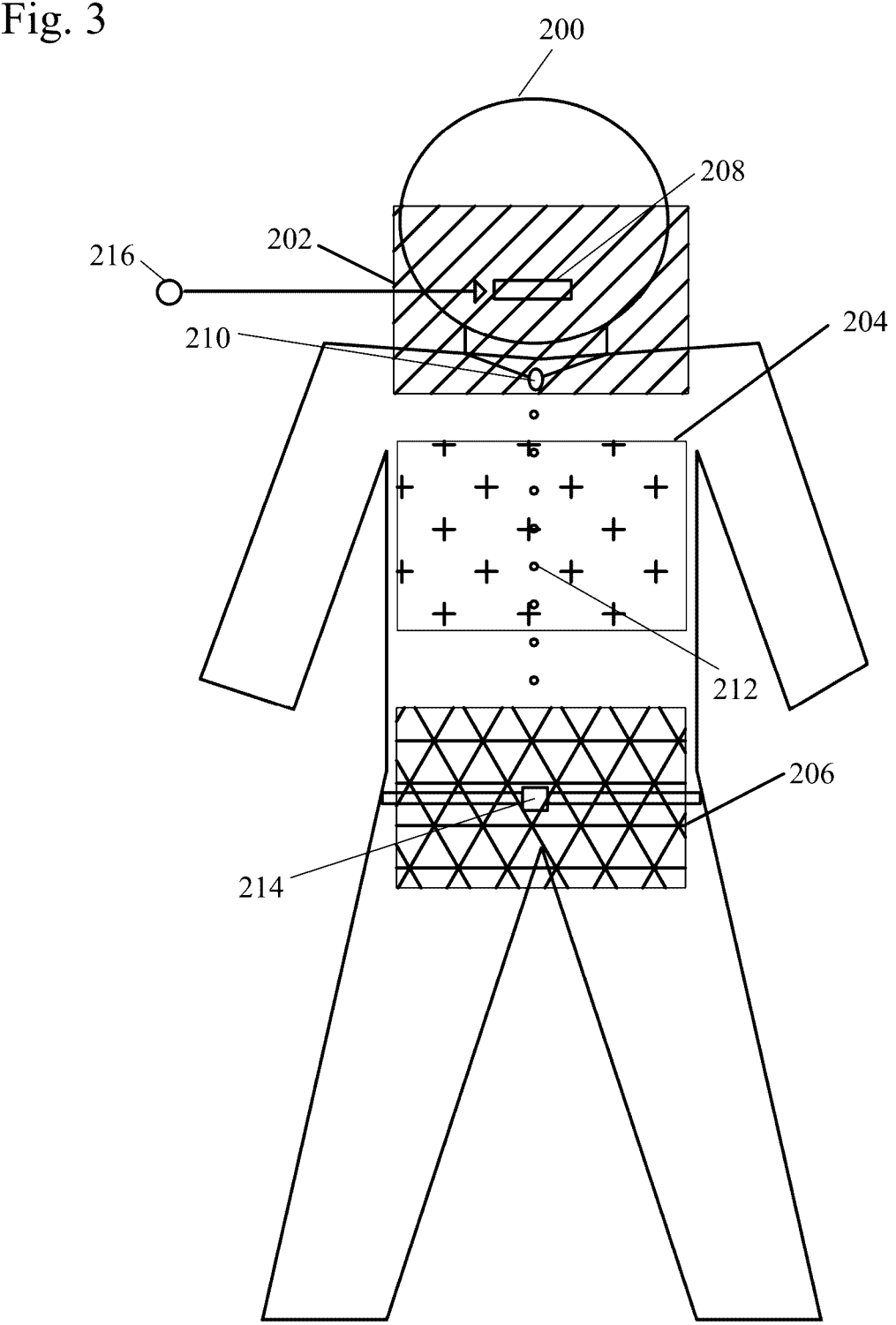
FIG. 3 shows a schematic of placement of sensors on a user.

Referring to FIG. 3, a first location of a first sensor may be present around the neck area of the user, shown by the diagonal lines and indicated by reference number 202. The first sensor can be worn on the body, for example around the neck, in an ear, or in some other area where the first sensor is able to detect an electronic tag in medication present in and around the mouth of a user 200.

A second location of a second sensor may be present around the upper torso, which is shown by the plus signs and indicated by reference number 204. The second sensor may be located in a button or a pendant or some other area which is able to detect the electronic tag in the medication as the medication is ingested.

A third sensor may be present around the lower torso, which is shown by the cross-hatching and indicated by reference number 206. The third sensor may be located in a button or a belt or present in a pocket of clothing worn by the user 200 or some other area which able to detect the electronic tag in the medication as it passes through the intestinal tract of the user and out of the body of the user.

While three locations were shown, additional locations may be used. Also, the method may be carried out using only two locations, a first location 202 and a second location 204 or a first location 202 and a third location 206.

The expected elapsed time between when an electronic tag in the medication should pass from a first location to a second location, a second location to a third location or a first location to a third location may be calibrated based on characteristics of the user.

The electronic tag present in the medication is preferably digestible, and the components of the tag should be inert and non-toxic. It should be noted that the communication between the sensors 55a-55n and electronic tag present within the medication may be such that the sensors detect a constant signal from an electronic tag or that the electronic tag sends an information signal in response to an interrogation signal from the sensor.

For example, each different type of medication may have a different unique RFID. The RFID tags may be passive. Passive RFID tags transmit a stream of information in response to an interrogation signal, such as an electromagnetic signal at a predetermined operating frequency. Passive RFID tags typically have no power source, and rely upon the energy delivered by the interrogation signal to transit the stream of information.

Alternatively, the RFID tags may be active. Active RFID tags may have a power source. Active RFID tags may transmit a stream of information on a continuous basis, a periodic basis, or in response to some external event.

Near field communication (NFC) may also be used to detect electronic tags.

Some of the sensors 55a-55n may act as receivers with directional antenna which can be individually polled by a main or detecting sensor. For example, the first sensor present in a pendant may poll the second sensor located in the shirt button and the third sensor located in the belt buckle worn by the user.

Alternatively, a device computer 52 (not shown in FIG. 3), may act as the receiver for each of the sensors 55a-55n, individually polling the sensors.

In a first step (step 102), a medication monitoring and notification program 66 receives medication identification from a first sensor at a first location of a user at a first time and stores the information in a repository. For example repository 53 of FIG. 1 or a repository or memory that may be present within each of the sensors themselves. The first location is preferably in the area of the mouth of the user. The information may also include dosage information.

The medication information is compared to the prescribed medication for the user (step 104) by the medication monitoring and notification program 66. If the dosage and/or medication is incorrect or does not match the medication and dosage prescribed for the user (step 106), a notification is sent to the user, for example through a device computer (step 108) and the method ends. The notification may identify the mismatch or incorrect medication/dosage for the user to an alternate user.

If the dosage and/or medication is correct and matches the medication and dosage prescribed for the user (step 106), a time threshold required for the medication to travel within the user from a first sensor location to another sensor location is determined (step 110). The time threshold required for the medication to travel may be a range of acceptable time in which it would take the medication to reach a location of another sensor. The signal strength of the electronic tag may also be determined.

For example and referring to FIG. 3, when the medication 216 is first taken by the user 200, only the first sensor 210 would be able to detect the electronic tag in the medication 216 in the first location 202. The signal from the electronic tag in the medication 216 detected by the first sensor 210 would be strong. As the medication 216 proceeds from the first location 202 to the second location 204, the first sensor 210 would be able to detect a weaker signal and the second sensor 212 would detect a stronger signal from the electronic tag in the medication 216 as it travels closer to the second sensor 212 and in the second location 204.

As the medication 216 travels from the second location 204 to the third location 206, the signal from the electronic tag in the medication 216 would be weaker for the second sensor 212, relatively non-existent for the first sensor 210 and stronger for the third sensor 214. Either one of the sensors or a device computer can precisely determine the location of the medication within the user using RFID signal strength, time of administration of the medication, and localization/mapping as well as RFID location using dual antennas.

If another sensor notification is not received (step 112) and the determined time threshold has been exceeded (step 114), a notification is sent to the user or alternate user (step 116) and the method ends. The notification may aid in an alternate user in identifying whether the user actually ingested the medication after the medication was placed in a mouth of the user.

If another sensor notification is not received (step 112) and the determined time has not passed (step 114), the method returns to step 112.

If another sensor notification was received (step 112), the signal strength and the time in which the other signal was received by the other sensor in the other location is compared to the determined time and signal strength based on the dosage of the medication and stored in a repository or memory of the sensor (step 118). The determined time and signal strength may include the signal strength detected from prior digestion of the medication by the user.

If the determined signal strength and/or time does not match the sensor notification (step 120), a notification is sent to the user and or the alternate user, for example through a device computer (step 122) and the method ends. The notification may aid in determining the absorption rate of the medication.

For example, if the signal strength is different than the signal strength during previous intake of the medication by the user, the difference in signal strength may be an indicator that the medication was damaged, for example due to pill splitting. The difference in signal strength may also indicate a blockage in the user's digestive track or other medical condition in which the user's body is flushing the medication from their body too quickly, for example, inflammatory bowel disease, irritable bowel syndrome, impaired function of the Vagus nerve, overactive thyroid gland, or diseases which interfere with food absorption and may give rise to emptying of the digestive tract very quickly or other medical possibilities. Some examples of the illnesses that interfere with food absorption are Celiac disease, lactose intolerance, pancreas malfunction, gallbladder trouble, inflammation of the digestive tract and other examples.

If the determined signal strength and/or time does match the sensor notification (step 120) and no other sensors are present (step 124), the method ends.

It should be noted that if additional sensors are being worn by the user (step 124) the method may return to step 110 until all of the sensors have detected the electronic tag or sent a notification to a user or alternate users.

The notification that is sent in steps 108, 116, 122 may be sent to just the user, sent to alternate users which monitor the care of the user, or both the user and the alternate users. The notification may be sent electronically for display on a computing device. The notification may be broadcasted to a television or other device in which the user can visually notified. Alternatively, the notification may be audibly delivered to the user.

The data generated and stored in a repository or memories from the sensors may analyzed at a later time by alternate users.

For example, a user may be wearing a first sensor in a first location 202 and a second sensor in a second location 204. The user may have been prescribed medication A at a dosage of 10 mg twice daily and medication B at a dosage of 300 mg four times daily. The first sensor detects an electronic tag in a medication that identifies the medication taken by the user as medication A, but at a dosage of 100 mg. The user or an alternate user is alerted on their computing device regarding the incorrect dosage ingested by the user. The alert may be sent by one of the sensors or alternatively by a device computer being worn by the user. Alternatively, the notification can be audibly provided to the user via a telephone call. Additionally, the notification can be provided visually on a television to the user.

In another example, a user may be wearing a first sensor in a first location 202 and another location in another location 206. The user may have been prescribed medication A at a dosage of 10 mg twice daily and medication B at a dosage of 300 mg four times daily. The first sensor detects an electronic tag in medications ingested that identifies the medications taken by the user as medication A, at a dosage of 10 mg and medication B at a dosage of 300 mg at 9:00 AM. Based on the user, the medications should be detected by the other location sensor within three hours of ingestion, at 12:00 PM. The time determination may be made by one of the sensors or alternatively a device computer being worn by the user. If the other sensor does not receive or detect a signal from the electronic tag of medication A and B between 11:30 AM and 12:30 PM, a notification is sent to the user and/or alternate user regarding the lack of sensor detection. This information can be used to determine whether the user just held the medication in their mouth and failed to ingest the medication.

In another example, a user may be wearing a first sensor in a first location 202 and another sensor in another location 206. The user may have been prescribed medication A at a dosage of 10 mg twice daily and medication B at a dosage of 300 mg four times daily. The first sensor detects an electronic tag in medications ingested that identifies the medications taken by the user as medication A, at a dosage of 10 mg and medication B at a dosage of 300 mg at 9:00 AM. Based on the user, the medications should be detected by the third location by 12:00 PM. At 12:00 PM, the other sensor receives or detects a signal for medication A but not medication B. A notification is sent to the user and/or alternate user regarding the lack of sensor detection of medication B. The time determination may be made by one of the sensors or alternatively a device computer being worn by the user. This information can be used to determine whether the user just held the medication in their mouth and failed to ingest the medication or perhaps a problem with ingesting medication B.

In another example, a user may be wearing a first sensor in a first location 202, another sensor in another location 206, and a wearable device computer 52. The user may have been prescribed medication A at a dosage of 10 mg twice daily. The first sensor detects an electronic tag in the medication ingested that identifies the medication taken by the user as medication A, at a dosage of 10 mg at 9:00 AM. The input from the sensors may be polled by the wearable device computer 52 at specific time intervals to determine a precise location of medication A, based on the signal strength relative to the sensors in the first location and the other location. Based on the user, medication A should be detected by the other location sensor within three hours of ingestion, at 12:00 PM. If the strength of the signal detected by the other location sensor is low at 12:00 PM, and no signal is present at the first sensor location, the medication may have caused a side effect which resulted in emptying of the digestive tract very quickly. This side effect may be sent to an alternate user.

FIG. 4 illustrates internal and external components of device computer 52 and server computer 54 in which illustrative embodiments may be implemented. In FIG. 4, device computer 52 and server computer 54 include respective sets of internal components 800*a*, 800*b* and external components 900*a*, 900*b*. Each of the sets of internal components 800*a*, 800*b* includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828, and medication monitor and notification program 66 are stored on one or more of the computer-readable tangible storage devices 830 for execution by one or more of the processors 820 via one or more of the RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800a, 800b also includes a R/W drive or interface 832 to read from and write to one or more portable computer-readable tangible storage devices 936 such as a CD-ROM, DVD, memory stick, magnetic tape, magnetic disk, optical disk or semiconductor storage device. Medication monitor and notification program 66 can be stored on one or more of the portable computer-readable tangible storage devices 936, read via R/W drive or interface 832 and loaded into hard drive 830.

Each set of internal components 800a, 800b also includes a network adapter or interface 836 such as a TCP/IP adapter card. Medication monitor and notification program 66 can be downloaded to the device computer 52 and server computer 54 from an external computer via a network (for example, the Internet, a local area network or other, wide area network) and network adapter or interface 836. From the network adapter or interface 836, medication monitor and notification program 66 is loaded into hard drive 830. The network may comprise copper wires, optical fibers, wireless transmission, routers, firewalls, switches, gateway computers and/or edge servers.

Each of the sets of external components 900a, 900b includes a computer display monitor 920, a keyboard 930, and a computer mouse 934. Each of the sets of internal components 800a, 800b also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Medication monitor and notification program 66 can be written in various programming languages including low-level, high-level, object-oriented or non object-oriented languages. Alternatively, the functions of a medication monitor and notification program 66 can be implemented in whole or in part by computer circuits and other hardware (not shown).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Having thus described the invention of the present application in detail and by reference to embodiments thereof, it will be apparent that modifications and variations are possible without departing from the scope of the invention defined in the appended claims.

What is claimed is:

1. A method of monitoring medication and administration of medication to a user containing edible electronic tags through the use of at least a first sensor at a first location and a second sensor at a second location different than the first location, the first sensor and second sensor each comprising: one or more memories, an electronic tag reader, and at least one antenna, at least one of the first and second sensors being coupled to communicate with a computer comprising: at least one processor, one or more memories, and a repository coupled to the processor, the method comprising the steps of:
   the computer receiving an identification of at least a medication and a time of administration of the medication to the user from the first sensor and storing the identification in the repository;
   the computer comparing the identification of the medication to prescribed medication for the user;
   the computer determining a time required for the medication to travel from the first location to the second location;
   the computer monitoring for the electronic tag at the second location until the determined time has passed or the electronic tag is identified;
   wherein when the determined time has passed and the electronic tag has not been identified, the computer sending a notification to at least one user; and
   wherein when the electronic tag is identified, the computer confirming ingestion of the medication by the user and storing the time and electronic tag identification to the repository.

2. The method of claim 1, wherein the notification is sent to an alternate user providing care of the user.

3. The method of claim 1, wherein the method further comprises the step of the computer determining a signal strength to be detected at the second location.

4. The method of claim 1, wherein communication between the electronic tag and the first sensor and second sensor is through radio-frequency identification.

5. The method of claim 1, wherein communication between the electronic tag and the first sensor and second sensor is through near field communication.

6. The method of claim 1, wherein the first or second sensor comprises the computer.

7. The method of claim 1, wherein the computer is separately wearable by the user in a location other than the first location and the second location.

8. A computer program product for monitoring medication and administration of medication to a user containing edible electronic tags through the use of at least a first sensor at a first location and a second sensor at a second location different than the first location, the first sensor and second sensor each comprising: one or more memories, an electronic tag reader, and at least one antenna, at least one of the first and second sensors being coupled to communicate with a computer comprising: at least one processor, one or more memories, and a repository coupled to the processor, a computer readable storage medium having program instructions embodied therewith, the program instructions executable by the computer to perform the method comprising:
   receiving, by the computer, an identification of at least a medication and a time of administration of the medication to the user from the first sensor and storing the identification in the repository;
   comparing, by the computer, the identification of the medication to prescribed medication for the user;
   determining, by the computer a time required for the medication to travel from the first location to the second location;
   monitoring, by the computer, for the electronic tag at the second location until the determined time has passed or the electronic tag is identified;
   wherein when the determined time has passed and the electronic tag has not been identified, the computer sending a notification to at least one user; and
   wherein when the electronic tag is identified, the computer confirming ingestion of the medication by the user and storing the time and electronic tag identification to the repository.

9. The computer program product of claim 8, wherein the notification is sent to an alternate user providing care of the user.

10. The computer program product of claim 8, wherein the computer program product further comprises program instructions of determining, by the computer, a signal strength to be detected at the second location.

11. The computer program product of claim 8, wherein communication between the electronic tag and the first sensor and second sensor is through radio-frequency identification.

12. The computer program product of claim 8, wherein communication between the electronic tag and the first sensor and second sensor is through near field communication.

13. The computer program product of claim 8, wherein the first or second sensor comprises the computer.

14. The computer program product of claim 8, wherein the computer is separately wearable by the user in a location other than the first location and the second location.

15. A computer system for monitoring medication and administration of medication to a user containing edible electronic tags through the use of at least a first sensor at a first location and a second sensor at a second location different than the first location, the first sensor and second sensor comprising: one or more memories, an electronic tag reader, and at least one antenna, at least one of the first and second sensors being coupled to communicate with a computer comprising: at least one processor, one or more memories, and a repository coupled to the processor, a computer readable storage medium having program instructions embodied therewith, the program instructions executable by the computer to perform the program instructions comprising:

receiving, by the computer, an identification of at least a medication and a time of administration of the medication to the user from the first sensor and storing the identification in the repository;

comparing, by the computer, the identification of the medication to prescribed medication for the user;

determining, by the computer a time required for the medication to travel from the first location to the second location;

monitoring, by the computer, for the electronic tag at the second location until the determined time has passed or the electronic tag is identified;

wherein when the determined time has passed and the electronic tag has not been identified, the computer sending a notification to at least one user; and wherein when the electronic tag is identified, the computer confirming ingestion of the medication by the user and storing the time and electronic tag identification to the repository.

16. The computer system of claim 15, wherein the notification is sent to an alternate user providing care of the user.

17. The computer system of claim 15, further comprising program instructions of determining, by the computer, a signal strength to be detected at the second location.

18. The computer system of claim 15, wherein communication between the electronic tag and the first sensor and second sensor is through radio-frequency identification.

19. The computer system of claim 15, wherein the first or second sensor comprises the computer.

20. The computer system of claim 15, wherein the computer is separately wearable by the user in a location other than the first location and the second location.

* * * * *